US008855940B2

(12) United States Patent
Vincent

(10) Patent No.: US 8,855,940 B2
(45) Date of Patent: *Oct. 7, 2014

(54) METHOD OF DETECTING COLIFORM BACTERIA FROM REFLECTED LIGHT

(71) Applicant: Bowling Green State University, Bowling Green, OH (US)

(72) Inventor: Robert K. Vincent, Bowling Green, OH (US)

(73) Assignee: Bowling Green State University, Bowling Green, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/787,785

(22) Filed: Mar. 6, 2013

(65) Prior Publication Data
US 2013/0337499 A1 Dec. 19, 2013

Related U.S. Application Data

(63) Continuation of application No. 10/762,952, filed on Jan. 22, 2004, now Pat. No. 8,417,460.

(51) Int. Cl.
G01N 33/48 (2006.01)
G01N 31/00 (2006.01)
G06G 7/48 (2006.01)
G06G 7/58 (2006.01)
G01N 21/31 (2006.01)
G01N 33/18 (2006.01)
C12Q 1/10 (2006.01)
G06F 19/10 (2011.01)

(52) U.S. Cl.
CPC .......... *C12Q 1/10* (2013.01); *G01N 2201/1293* (2013.01); *G06F 19/10* (2013.01); *G01N 21/31* (2013.01); *G01N 33/18* (2013.01)
USPC .................... 702/19; 702/22; 703/11; 703/12

(58) Field of Classification Search
CPC .................. G01N 21/31; G01N 33/18; G01N 2201/1293; G01J 3/427; C12Q 1/06; C12Q 1/689
See application file for complete search history.

(56) References Cited

PUBLICATIONS

Development and Spatial Distribution of an Algal Bloom in the Dead Sea: A Remote Sensing Study; Aquatic Microbial Ecology, (1997), Oren, A., et al., vol. 13: 219-223.
Phycocyanin Detection From Landsat TM Data for Mapping Cyanobacterial Blooms in Lake Erie; Remote Sensing of Environment, (2004), Vincent, R., et al. vol. 89: 381-392.
Detecting Trichodesmium Blooms in Seawifs Imagery; Deep-Sea Research II, (2002), Subramaniam, et al., 49, 107-121.
Determination of Water Quality Parameters Using Imagin Spectrometry (Case study for the Sajo floodplain, Hungary), Master's Thesis, International Institute for Geo-information Science and Earth Observation, Enschede, The Netherlands, Mar. 2003, Turkukulov, 1-78.
Movement and Persistence of Fecal Bacteria in Agricultural Soils and Subsurface Drainage Water: A Review, Canadian Biosystems Engineering, (2002), Jamieson, et al., 44:1.1-1.19.
DET110-High-Speed Silicon Dector, 2199-S01 Rev B, (2002), Thorlabs, Inc., 1-2.

*Primary Examiner* — Larry D Riggs, II
(74) *Attorney, Agent, or Firm* — Marshall & Melhorn, LLC

(57) ABSTRACT

The present invention relates to a method of detecting coliform bacteria in water from reflected light, and also includes devices for the measurement, calculation and transmission of data relating to that method.

15 Claims, 21 Drawing Sheets
(20 of 21 Drawing Sheet(s) Filed in Color)

Total Coliform Model from LANDSAT 7 TM Data and Water Samples Collected from Lake Erie on August 21, 2001

LANDSAT 7 TM Natural Color (Rt.) and Total Coliform (Left, Aug. 21, 2001 Model) Images (Redder is Greater) of SW Lake Erie (July 1, 2000 LANDSAT TM Data)

Department of Geology
Bowling Green State University

Coliform Mapping (Red means more) from LANDSAT TM: Subarea 2, Maumee Bay (Toledo and Maumee, OH)

Department of Geology
Bowling Green State University

Coliform Mapping (Red means more) from LANDSAT TM: Subarea 3, Upper Maumee (Waterville, OH)

Department of Geology
Bowling Green State University

Coliform Mapping (Red means more) from LANDSAT TM: Subarea 4, Low. Mid. Maumee (Grand Rapids, OH)

Department of Geology
Bowling Green State University

Coliform Mapping (Red means more) from LANDSAT TM: Subarea 5, Up. Mid. Maumee (Napoleon, OH)

Department of Geology
Bowling Green State University

Coliform Mapping (Red means more) from LANDSAT TM: Subarea 6, Lower Maumee (Defiance, OH)

Department of Geology
Bowling Green State University

Coliform Mapping (Red means more) from LANDSAT TM: Sandusky Bay, with Portage River in Image Center Department of Geology
Bowling Green State University Coliform Mapping (Red means more) from LANDSAT TM: Subarea 7, Oak Harbor, OH on the Portage River Department of Geology
Bowling Green State University Total Coliform Model of Aug. 21, 2001 Applied to Water Samples Collected from Maumee and Portage Rivers on Oct. 8, 2000

E. Coli Model from City of Oregon Data and LANDSAT TM Data Collected on Aug. 21, 2001 (Samples from All Water Depths)

E. Coli Model from the City of Oregon, Ohio Data in Maumee Bay for Aug. 21, 2001, for Samples from >6 ft. and >27 ft. Water Depths E. Coli Model (>6ft. Water Depth) of Oregon Water Samples Collected on Aug. 21, 2001 Applied to Water Samples Collected from Maumee and Portage Rivers on Oct. 8, 2000

Total Coliform (Left) and E. Coli (Right) Models of Aug. 21, 2001 from Lake Erie and Oregon, OH Data Applied to LANDSAT TM Data of Same Date Department of Geology
Bowling Green State University Zoomed E. Coli Images of Portage and Sandusky Rivers of Aug. 21, 2001

LANDSAT TM Data

Department of Geology
Bowling Green State University

Natural Color Image of Lake Erie on 16 July 2002 (Including Cleveland, Ohio)

Department of Geology
Bowling Green State University

Coliform Bacteria
(16 July 2002 Overpass,
21 August 2001 Model)

| Color | Coliform Bacterial Colonies Per 1 ml of Water |
|---|---|
| Red | 210-1060 |
| Yellow | 173-209 |
| Yellow-green | 110-134 |
| Blue-Green | 60-109 |
| Blue | 1-59 |
| Darkest Blue | 0 (Land) |

Department of Geology
Bowling Green State University

Natural Color Image of P. 19, R. 31 for 2 August 2002 L7 Overpass

Department of Geology
Bowling Green State University

Coliform Bacteria
August 2, 2002 Overpass
(21 August 2001 Model)

| Color | Coliform Bacterial Colonies Per 1 ml of Water |
|---|---|
| Red | 401-1710 |
| Yellow-Orange | 231-400 |
| Yellow-green | 202-230 |
| Blue-Green | 104-201 |
| Blue | 1-103 |
| Darkest Blue | 0 (Land) |

Department of Geology
Bowling Green State University

Coliform Bacteria for 2 August 2002 Overpass (16 July 2002 Stretch)

| Color | Coliform Bacterial Colonies Per 1 ml of Water |
|---|---|
| Red | 210-1060 |
| Yellow | 173-209 |
| Yellow-green | 110-134 |
| Blue-Green | 60-109 |
| Blue | 1-59 |
| Darkest Blue | 0 (Land) |

Department of Geology
Bowling Green State University

Coliform Bacteria for July 16, 2002 (Left) and August 2, 2002 (Right) Overpasses, Path 20-Row 31
(21 August 2001 Model; red represents 210-1710 colonies/ml in both images)

Department of Geology
Bowling Green State University

METHOD OF DETECTING COLIFORM BACTERIA FROM REFLECTED LIGHT

CROSS-REFERENCE TO RELATED APPLICATIONS

This application is a continuation of and, pursuant to 35 U.S.C. §120, claims the benefit of U.S. patent application Ser. No. 10/762,952, filed on Jan. 22, 2004, which is pending as of the filing date of this application. Application Ser. No. 10/762,952 is hereby incorporated by reference in its entirety.

STATEMENT REGARDING GOVERNMENTAL INTEREST

The present invention was made through funding from grant number NAG3-2629 from the National Aeronautical and Space Administration (NASA) to through the Ohio Aerospace Institute (OAI) as fiduciary agent. The United States Government has certain rights in the invention.

BACKGROUND OF THE INVENTION

The present invention relates to a method of detecting coliform bacteria in water from reflected light.

In many instances it is desirable to be able to detect the presence microorganisms in water, particularly bodies of water that serve as a source for drinking water or that may serve as a site for recreation, such as for swimming boating, water sports and fishing. Many of these organisms in high concentrations can be harmful to the public and to the environment generally.

It is particularly desirable to be able to be able to detect the presence microorganisms in water in a manner that is convenient and provides relatively immediate results so that the public may be warned or other actions taken to avoid or eliminate contamination of the assayed water.

In addition to the features mentioned above, objects and advantages of the present invention will be readily apparent upon a reading of the following description and through practice of the present invention.

SUMMARY OF THE INVENTION

In general terms, the present invention includes a method of determining the presence of coliform bacteria in water as well as a measurement method followed by transmission of data to a remote processing site.

The invention includes a method of determining the presence of coliform bacteria in water from light reflected therefrom. The method comprises the steps of: (a) obtaining a measurement of reflected light from the water, the measurement comprising a measurement of the respective amount of light in at least three frequency ranges; and (b) relating the approximate amount of coliform in the water to the respective amounts of light by applying an algorithm relating the respective amounts of light in the at least three frequency ranges to the amount of coliform bacteria in the water.

It is preferred that the at least three frequency ranges are all in the visible-reflective IR range. It is also preferred that the at least three frequency ranges are all within the detectable range of a silicon detector such that silicon based cameras or detectors might be used for the reflected light uptake.

In a preferred embodiment, the measurement of reflected light from the water, the measurement comprising a measurement of the respective amount of light in at least three frequency ranges (i) from about 0.53 µm to about 0.60 µm; (ii) from about 0.63 µm to about 0.69 µm; and (iii) from about 0.76 µm to about 0.90 µm; and (b) relating the approximate number of the coliform in the water to the respective amounts of light by applying an algorithm relating the respective amounts of light in the at least three frequency ranges to the amount of coliform bacteria in the water.

Preferably, the measurement of the amount of light in the at least three frequency ranges comprises the measurement, respectively, of: (i) LANDSAT Thematic Mapper ("TM") band 2, (ii) LANDSAT TM band 3 and (iii) LANDSAT TM band 4. The measurement of the amount of light in the at least three frequency ranges may optionally comprise the measurement, respectively, of: (i) LANDSAT TM band 2, (ii) LANDSAT TM band 3 and (iii) LANDSAT TM band 4, and where the algorithm is any algorithm selected from the group consisting of: $X \approx K_1 + K_2 \times (R32) + K_3 \times (R43)$ and equivalents wherein:

X is the approximate amount of coliform bacteria expressed in colonies per milliliter;
$K_1$ is a value in the range of from about $-175$ to about $-350$;
$K_2$ is a value in the range of from about 250 to about 350;
$K_3$ is a value in the range of from about 200 to about 350;
R32 is the value of LANDSAT TM band 3 divided by LANDSAT TM band 2, after subtraction for atmospheric haze separately in each band; and
R43 is the value of LANDSAT TM band 4 divided by LANDSAT TM band 3, after subtraction for atmospheric haze separately in each band.

More preferably, these ranges may be as follows:
X is the amount of coliform bacteria expressed in colonies per milliliter;
$K_1$ is a value in the range of from about $-200$ to about $-300$;
$K_2$ is a value in the range of from about 275 to about 325;
$K_3$ is a value in the range of from about 225 to about 275;
R32 is the value of the amount of light of LANDSAT TM band 3 divided by the value of the amount of light of LANDSAT TM band 2, after subtraction for atmospheric haze separately in each band; and
R43 is the value of the amount of light of LANDSAT TM band 4 divided by the value of the amount of light of LANDSAT TM band 3, after subtraction for atmospheric haze separately in each band.

Most preferably, these ranges may be as follows:
X is the amount of coliform bacteria expressed in colonies per milliliter;
$K_1$ is a value in the range of from about $-265$ to about $-275$;
$K_2$ is a value in the range of from about 300 to about 320;
$K_3$ is a value in the range of from about 225 to about 275;
R32 is the value of the amount of light of LANDSAT TM band 3 divided by the value of the amount of light of LANDSAT TM band 2, after subtraction for atmospheric haze separately in each band; and
R43 is the value of the amount of light of LANDSAT TM band 4 divided by the value of the amount of light of LANDSAT TM band 3, after subtraction for atmospheric haze separately in each band.

The method according to the present invention is such that the calculated value of coliform (X) correlates to the actual measured amount of the coliform in the water by a correlation value in excess of 60% and as high as in excess of 80%.

The present invention may additionally comprise the step of generating a report of the approximate number of the coliform colonies per ml in the water. This may be done using electronics adapted to digitize and process the data using an appropriate algorithm, such as that described herein. For instance, the report may include an estimate of the number of the coliform colonies per ml in the water.

The method of the present invention may also include the step of transmitting data relating to the approximate number of the coliform colonies per mL in the water to a site remote from the site where the measurement takes place. This may be done using any transmission method including land line or wireless transmission. This is also used advantageously where the reflected light is sensed remotely by aircraft, satellite, boat or buoy. Processing of the data may take place at the site of light uptake or may be carried out at a remote location after transmission of the raw data. The estimated coliform report may be sent to public authorities, such as police departments, fire and rescue departments or life guard services to warn swimmers, boaters, sportsman or the public at large that a given body of water, or portion thereof, likely contains elevated/dangerous levels of coliform.

The invention also includes an apparatus for determining the presence of coliform bacteria in water from light reflected therefrom, the device comprising: (a) a measurement device adapted to measure reflected light from the water, the measurement comprising a measurement of the respective amount of light in at least three frequency ranges (i) from about 0.53 μm to about 0.60 μm; (ii) from about 0.63 μm to about 0.69 μm; and (iii) from about 0.76 μm to about 0.90 μm; and (b) a processor capable of relating the approximate number of coliform in the water to the respective amounts of light by applying an algorithm relating the respective amounts of light in the at least three frequency ranges to the amount of coliform bacteria in the water.

It is preferred that the apparatus has a measurement device wherein the at least three frequency ranges are all in the visible range. It is also preferred that the at least three frequency ranges are all within the detectable range of a silicon detector, and wherein the measurement device comprises a silicon detector. Most preferably, the at least three frequency ranges comprise, respectively: (i) LANDSAT TM band 4, (ii) LANDSAT TM band 3 and (iii) LANDSAT TM band 2, such as (i) LANDSAT TM band 4, (ii) LANDSAT TM band 3 and (iii) LANDSAT TM band 2, and wherein the algorithm is any algorithm selected from the group consisting of: $X \approx K_1 + K_2 \times (R32) + K_3 \times (R43)$ wherein:

X is the approximate amount of coliform bacteria expressed in colonies per milliliter;

$K_1$ is a value in the range of from about −175 to about −350;
$K_2$ is a value in the range of from about 250 to about 350;
$K_3$ is a value in the range of from about 200 to about 350;
R32 is the value of LANDSAT TM band 3 divided by LANDSAT TM band 2; and
R43 is the value of LANDSAT TM band 4 divided by LANDSAT TM band 3;

and preferably wherein:

X is the amount of coliform bacteria expressed in colonies per milliliter;

$K_1$ is a value in the range of from about −200 to about −300;
$K_2$ is a value in the range of from about 275 to about 325;
$K_3$ is a value in the range of from about 225 to about 275;
R32 is the value of the amount of light of LANDSAT TM band 3 divided by the value of the amount of light of LANDSAT TM band 2; and
R43 is the value of the amount of light of LANDSAT TM band 4 divided by the value of the amount of light of LANDSAT TM band 3.

and most preferably wherein:

X is the amount of coliform bacteria expressed in colonies per milliliter;

$K_1$ is a value in the range of from about −265 to about −275;
$K_2$ is a value in the range of from about 300 to about 320;
$K_3$ is a value in the range of from about 225 to about 275;
R32 is the value of the amount of light of LANDSAT TM band 3 divided by the value of the amount of light of LANDSAT TM band 2; and
R43 is the value of the amount of light of LANDSAT TM band 4 divided by the value of the amount of light of LANDSAT TM band 3.

It is preferred that the apparatus is capable of performing such that the calculated value of coliform correlates to the actual measured amount of the coliform in the water by a correlation value in excess of 60, and most preferably by a correlation value in excess of 80.

The apparatus may additionally include a report generator adapted to generate a report of the approximate amount of coliform in the water. Such a report generator may be any device that is adapted to place the data into a tangible medium, such as a printer, CD burner, flash memory, magnetic storage media, etc.

The apparatus may additionally include a transmitter adapted to transmit data relating to the approximate amount of the coliform in the water from the processor to a site remote from the site where the measurement takes place. Such a transmitter may include those adapted to send data such as through land line or wireless transmission, including telephone, internet, cell phone, radio and the like.

The measurement device may be any device adapted to sense and record and/or transmit the light frequencies described above. Examples include photosensors, cameras, digital cameras and video cameras, etc.

The processor may be any data processing device having programming instructions for applying the algorithm, such as preferably a microprocessor.

It is preferred that the algorithm comprises a linear relationship between the approximate amount of the coliform in the water and sum of (a) the ratio of the first frequency to the second frequency and (b) the ratio of the second frequency to the third frequency.

The measurement device may be placed in any position from which it can sense the required light frequencies, such as on a buoy, a boat, a light house or similar dedicated tower structure, an elevated lifeguard house. The measurement device may also be in the form of a handheld device, such as a camera connected to a processor for processing the recorded light frequencies, the device may also be in the form of a device similar to a personal digital assistant with light recording and processing functions.

Another variation of the invention is a system using transmission of light measurement data to processor at a different location, recognizing that the processing may be done at a different location than the light sensing/recording.

In general terms, this variation is a system for determining the presence of coliform bacteria in water from light reflected therefrom, the device comprising (a) a measurement device adapted to measure reflected light from the water, the measurement comprising a measurement of the respective amount of light in at least three frequency ranges (i) from about 0.53 μm to about 0.60 μm; (ii) from about 0.63 μm to about 0.69 μm; and (iii) from about 0.76 μm to about 0.90 μm; and (b) a processor at the remote site and capable of relating the approximate number of the coliform in the water to the respective amounts of light by applying an algorithm relating the respective amounts of light in the at least three frequency ranges to the amount of coliform bacteria in the water.

The invention also includes a method of developing an apparatus for determining the presence of coliform bacteria in water from light reflected therefrom, the device comprising (a) obtaining a measurement of reflected light from the water, the measurement comprising a measurement of the respective amount of light of at least two frequencies; (b) developing an algorithm relating the respective amounts of light in the at least two frequencies to the amount of coliform bacteria in the water through linear regression analysis; (c) producing a processor capable of relating the approximate number of the coliform in the water to the respective amounts of light by applying an algorithm relating the respective amounts of light in the at least three frequency ranges to the amount of coliform bacteria in the water; and (d) providing a measurement device adapted to measure reflected light from the water and adapted to provide data relating to the measurement to the processor.

It is preferred that the at least two frequencies are all in the visible range, and that the at least two frequencies are all within the detectable range of a silicon detector. It is also preferred that the at least two frequencies comprises a LANDSAT TM band, and most preferably comprises a measurement of LANDSAT TM band 4, LANDSAT TM band 3 and LANDSAT TM band 2.

The present invention also includes methods and devices similar to those described above, and that use a specific algorithm for estimating the amount of E. Coli in water.

In general, this variation of the invention includes a method of determining the presence of E. Coli in water from light reflected therefrom, the method comprising the steps of: (a) obtaining a measurement of reflected light from the water, the measurement comprising a measurement of the respective amount of light in at least three frequency ranges: (i) from about 0.52 μm to about 0.60 μm; (ii) from about 0.76 μm to about 0.90 m; and (iii) from about 1.55 μm to about 1.75 μm; and (b) relating the approximate number of the E. Coli colonies in the water to the respective amounts of light by applying an algorithm relating the respective amounts of light in the at least three frequency ranges to the amount of E. Coli colonies in the water.

The three or more frequency ranges are preferably all in the visible-reflective IR range, and most preferably are: (i) LANDSAT TM band 2, (ii) LANDSAT TM band 4, and (iii) LANDSAT TM band 5.

The algorithm may be selected from any algorithm selected from the group consisting of $X \approx K_1 + K_2 \times (R42) - K_3 \times (R52) + K_4 \times (R54)$ and its mathematical equivalents wherein:

$X$ is the approximate amount of E. Coli expressed in colonies per 100 ml;

$K_1$ is a value in the range of from about −220 to about −420;
$K_2$ is a value in the range of from about 1750 to about 1950;
$K_3$ is a value in the range of from about 1130 to about 1330;
$K_4$ is a value in the range of from about 100 to about 300;
R42 is the value of LANDSAT TM band 4 divided by LANDSAT TM band 2, after subtraction for atmospheric haze separately in each band; R52 is the value of LANDSAT TM band 5 divided by LANDSAT TM band 2, after subtraction for atmospheric haze separately in each band; and R54 is the value of LANDSAT TM band 5 divided by LANDSAT TM band 4, after subtraction for atmospheric haze separately in each band.

These values are preferably:
$K_1$ is a value in the range of from about −300 to about −400;
$K_2$ is a value in the range of from about 1825 to about 1875;
$K_3$ is a value in the range of from about 1170 to about 1290;
$K_4$ is a value in the range of from about 175 to about 250;
and are most preferably:
$K_1$ is a value in the range of from about −310 to about −330;
$K_2$ is a value in the range of from about 1860 to about 1870;
$K_3$ is a value in the range of from about 1220 to about 1250; and
$K_4$ is a value in the range of from about 200 to about 220.

Estimations done by this method achieve calculated estimate values of E. Coli that correlates to the actual measured amount of the E. Coli in the water by a correlation value in excess of 60%, and as high as in excess of 70%.

The method of the present invention may also include the step of generating a report of the approximate amount of the E. Coli The method may also include the step of transmitting data relating to the approximate amount of the E. Coli in the water to a site remote from the site where the measurement takes place either before of after the calculations are performed.

A preferred embodiment of the present invention includes a method of determining the presence of E. Coli in water from light reflected therefrom, the method comprising the steps of: (a) obtaining a measurement of reflected light from the water, the measurement comprising a measurement of the respective amount of light in at least three frequencies comprising, respectively: (i) LANDSAT TM band 2, (ii) LANDSAT TM band 4, and (iii) LANDSAT TM band 5; and (b) relating the approximate amount of the E. Coli in the water to the respective amounts of light by applying an algorithm relating the respective amounts of light in the at least three frequency ranges to the amount of E. Coli in the water, wherein the algorithm is any algorithm selected from the group consisting of $X \approx K_1 + K_2 \times (R42) - K_3 - (R52) + K_4 \times (R54)$ and equivalents wherein:

$X$ is the approximate amount of E. Coli expressed in colonies per 100 ml;

$K_1$ is a value of about −321;
$K_2$ is a value of about 1864;
$K_3$ is a value of about 1235;
$K_4$ is a value of about 213;
R42 is the value of LANDSAT TM band 4 divided by LANDSAT TM band 2, after subtraction for atmospheric haze separately in each band;
R52 is the value of LANDSAT TM band 5 divided by LANDSAT TM band 2, after subtraction for atmospheric haze separately in each band; and
R54 is the value of LANDSAT TM band 5 divided by LANDSAT TM band 4, after subtraction for atmospheric haze separately in each band.

The present invention also includes a method that involves transmitting the spectral data before the algorithm is applied, which involves the steps of: (a) obtaining a measurement of reflected light from the water, the measurement comprising a measurement of the respective amount of light in at least three frequency ranges: (i) from about 0.52 μm to about 0.60 μm; (ii) from about 0.76 μm to about 0.90 m; and (iii) from about 1.55 μm to about 1.75 μm; (b) transmitting data relating to the measurement to a site remote from the measurement device; and (c) relating the approximate number of the E. Coli Expressed in micrograms per liter in the water to the respective amounts of light at the remote site by applying an algorithm relating the respective amounts of light in the at least three frequency ranges to the amount of E. Coli in the water.

The present invention also includes an apparatus for detecting and estimating the amount of E. Coli from reflected light, the apparatus comprising: a measurement device adapted to measure reflected light from the water, the measurement comprising a measurement of the respective amount of light in at least three frequency ranges: (i) from about 0.52 μm to about 0.60 μm; (ii) from about 0.76 μm to about 0.90 m; and (iii) from about 1.55 μm to about 1.75 μm; and a processor capable of relating the approximate number of the E. Coli in the water to the respective amounts of light by applying an algorithm relating the respective amounts of light in the at least three frequency ranges to the amount of E. Coli in the water.

Preferably, the measurement of the amount of light in the at least three frequency ranges comprises the measurement, respectively, of: (i) LANDSAT TM band 2, (ii) LANDSAT TM band 4, and (iii) LANDSAT TM band 5.

The preferred algorithm is any algorithm selected from the group consisting of: $X \approx K_1 + K_2 \times (R42) - K_3 \times (R52) + K_4 \times (R54)$ and equivalents wherein:

X is the approximate amount of *E. Coli* expressed in colonies per 100 ml;

$K_1$ is a value in the range of from about −220 to about −420;

$K_2$ is a value in the range of from about 1750 to about 1950;

$K_3$ is a value in the range of from about 1130 to about 1330;

$K_4$ is a value in the range of from about 100 to about 300;

R42 is the value of LANDSAT TM band 4 divided by LANDSAT TM band 2, after subtraction for atmospheric haze separately in each band;

R52 is the value of LANDSAT TM band 5 divided by LANDSAT TM band 2, after subtraction for atmospheric haze separately in each band; and R54 is the value of LANDSAT TM band 5 divided by LANDSAT TM band 4, after subtraction for atmospheric haze separately in each band.

The preferred values of the R and K values are as given above.

The apparatus may also include a report generator adapted to generate a report of the approximate amount of the *E. Coli* in the water. The apparatus may also include a transmitter adapted to transmit data relating to the approximate amount of the *E. Coli* in the water from the processor to a site remote from the site where the measurement takes place.

The measurement device may be a camera, and the processor may be a microprocessor having programming instructions for applying the algorithm. Preferably the algorithm will comprise a linear relationship between the approximate number of the *E. Coli* in the water and sum of (a) the ratio of the first frequency to the second frequency and (b) the ratio of the second frequency to the third frequency.

The apparatus may be mounted anywhere where reflected light may be gather, such as on a ship, a buoy, a shore tower, an airplane, weather balloon or drone.

The apparatus may be made to a size that can be conveniently handheld using known miniaturization techniques and materials.

A preferred apparatus of the present invention comprises:

(a) a measurement device adapted to measure reflected light from the water, the measurement comprising a measurement of the respective amount of light in at least four frequencies comprising, respectively: (i) LANDSAT TM band 2, (ii) LANDSAT TM band 4, and (iii) LANDSAT TM band 5; and (b) a processor capable of relating the approximate number of the *E. Coli* in the water to the respective amounts of light by applying an algorithm relating the respective amounts of light in the at least three frequency ranges to the amount of *E. Coli* in the water, wherein the algorithm is any algorithm selected from the group consisting of: $X \approx K_1 + K_2 \times (R42) - K_3 \times (R52) + K_4 \times (R54)$ and equivalents wherein:

X is the approximate amount of *E. Coli* expressed in colonies per 100 ml;

$K_1$ is a value in the range of from about −220 to about −420;

$K_2$ is a value in the range of from about 1750 to about 1950;

$K_3$ is a value in the range of from about 1130 to about 1330;

$K_4$ is a value in the range of from about 100 to about 300;

R42 is the value of LANDSAT TM band 4 divided by LANDSAT TM band 2, after subtraction for atmospheric haze separately in each band;

R52 is the value of LANDSAT TM band 5 divided by LANDSAT TM band 2, after subtraction for atmospheric haze separately in each band; and R54 is the value of LANDSAT TM band 5 divided by LANDSAT TM band 4, after subtraction for atmospheric haze separately in each band.

The present invention also includes a system for determining the presence of *E. Coli* in water from light reflected therefrom, the system comprising: (a) a measurement device adapted to measure reflected light from the water, the measurement comprising a measurement of the respective amount of light in at least three frequency ranges: (i) from about 0.52 µm to about 0.60 µm; (ii) from about 0.76 µm to about 0.90 m; and (iii) from about 1.55 µm to about 1.75 µm; and (b) a processor at the remote site and capable of relating the approximate amount of the *E. Coli* in the water to the respective amounts of light by applying an algorithm relating the respective amounts of light in the at least three frequency ranges to the amount of *E. Coli* in the water.

The present invention also includes a method of developing an apparatus for determining the presence of *E. Coli* in water from light reflected therefrom, the device comprising: (a) obtaining a measurement of reflected light from the water, the measurement comprising a measurement of the respective amount of light of at least two frequencies; (b) developing an algorithm relating the respective amounts of light in the at least two frequencies to the amount of *E. Coli* in the water through linear regression analysis; (c) producing a processor capable of relating the approximate number of the *E. Coli* in the water to the respective amounts of light by applying an algorithm relating the respective amounts of light in the at least three frequency ranges to the amount of *E. Coli* in the water; and (d) providing a measurement device adapted to measure reflected light from the water and adapted to provide data relating to the measurement to the processor.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Novel features and advantages of the present invention, in addition to those mentioned above, will become apparent to those skilled in the art from a reading of the following detailed description in conjunction with the accompanying drawings summarized as follows.

DETAIL DESCRIPTION OF PREFERRED EMBODIMENT(S)

Figure 1:
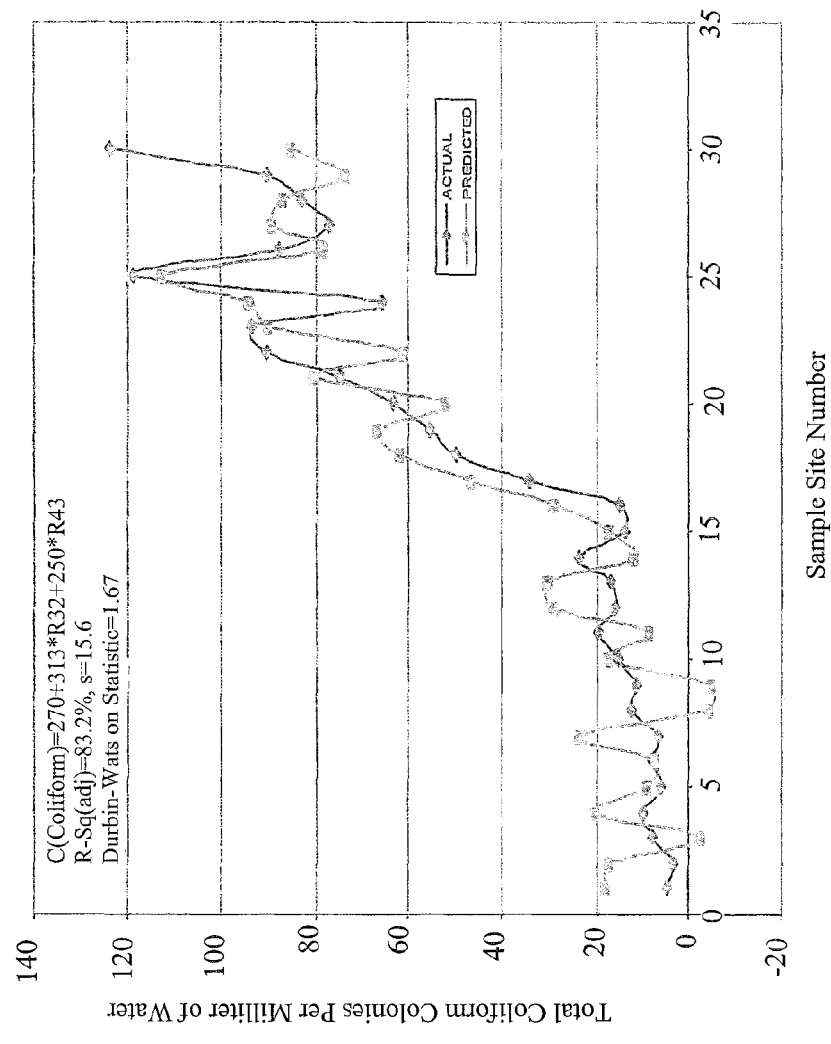
FIG. 1 is a graph illustrating the total coliform model from LANDSAT 7 TM data and water samples collected from Lake Erie as taken using one embodiment of the present invention.

The preferred system herein described is not intended to be exhaustive or to limit the invention to the precise forms disclosed. They are chosen and described to explain the principles of the invention and the application of the method to practical uses so that others skilled in the art may practice the invention.

The present invention includes a system using an algorithm for converting LANDSAT TM multispectral signals into images showing different values of Coliform (including E. coli bacteria) colonies per milliliter of water. This system and method were tested in Lake Erie and its wider tributaries detect coliform bacteria in the waters of Lake Erie to analyze the changes in water populations as they affect human activities. By gathering water samples during the period of time the satellite passes over Lake Erie and applying test kits, the level of coliform populations was determined. The preferred algorithm combines 2 ratios of three of the six spectral bands within silicon detector range (one to determine chlorophyll and the other turbidity).

The method of the present invention may be carried out using any sensing appropriate light sensing devices adapted to capture the algorithm-relevant frequencies as described herein, including satellite and surface sensors (such as a wireless multispectral coliform detector, or WIMCOD) for detection of coliform and E. coli bacteria.

An algorithm that may be used in the present invention, which may be carried out by computer instructions for producing a particular type of image that can be used to map a particular substance from a remote sensing platform in space, in an aircraft, or on the ground, may be determined as follows.

LANDSAT Thematic Mapper (TM) is a sensor that has 8 spectral bands, 6 of which have a 30-meter spatial resolution and which detect visible and infrared radiation (sunlight) reflected off the Earth's surface. The following bands were employed, with the wavelength limits (in micrometers, or μm) of their spectral band-widths given below for the LANDSAT 7 version of TM, called ETM+, and the LANDSAT 4 and 5 versions, called TM:

TABLE 1

TM and ETM+ Spectral Bandwidths
Bandwidth (μ) Full Width-Half Maximum

| Sensor | Band 1 Plot Data | Band 2 Plot Data | Band 3 Plot Data | Band 4 Plot Data | Band 5 Plot Data | Band 6 Plot Data | Band 7 Plot Data | Band 8 Plot Data |
|---|---|---|---|---|---|---|---|---|
| TM | 0.45-0.52 | 0.52-0.60 | 0.63-0.69 | 0.76-0.90 | 1.55-1.75 | 10.4-12.5 | 2.08-2.35 | N/A |
| ETM+ | 0.45-0.52 | 0.53-0.61 | 0.63-0.69 | 0.78-0.90 | 1.55-1.75 | 10.4-12.5 | 2.09-2.35 | .52-.90 |

For instance, band 2 of the LANDSAT 7 version of the TM sensor (called ETM+) has wavelength limits of 0.53-0.61 μm, band 3 has limits of 0.63-0.69 μm, and band 4 has limits of 0.78-0.90 μm. When mapping phycocyanin pigment, coliform bacteria, and E. coli bacteria in Lake Erie and its tributaries with LANDSAT 7 data, it had to be determined which or how many of bands 1-5 and 7 (which have 30-m spatial resolution and relatively narrow spectral bands, as opposed to the 60-m spatial resolution of band 6 and the relatively wide band-width of the 15-m-resolution band 8) to use. A mathematical procedure (multiple regressions) was applied to seek the best combinations of those bands to correlate with each one of these targets (phycocyanin, coliform, and E. coli) separately. It was determined that the use of the single band radiances (even if they were reduced to spectral reflectances from theoretical atmospheric models) as inputs to this procedure, the resulting algorithm would not be very robust (i.e., repeatable under different solar illumination and atmospheric conditions). Therefore, spectral ratios (ratios of spectral bands, after empirical correction for atmospheric haze through a process referred to as "dark object subtraction" were input to the mathematical procedure for each pixel from which a water sample had been collected. These 15 non-reciprocal ratios (R21, R31, R32, R41, . . . R75) became the dependent variables and phycocyanin (or coliform or *E. coli*) became the independent variable, which was the result of lab analysis of the water samples. For the LANDSAT 7 overpass, 30 water samples were collected, which were measured for both phycocyanin and coliform content. The best subsets of spectral ratios were determined, and then the ones with the highest $R^2$ (Adjusted) values were tested to see if they passed the Durbin-Watson test. The model with the highest $R^2$ (Adjusted) that also passed the Durbin-Watson test was the model that was considered to be the best.

FIG. 1 is a graph illustrating the total coliform model from LANDSAT 7 TM data and water samples collected from Lake Erie as taken using one embodiment of the present invention.

Figure 2:
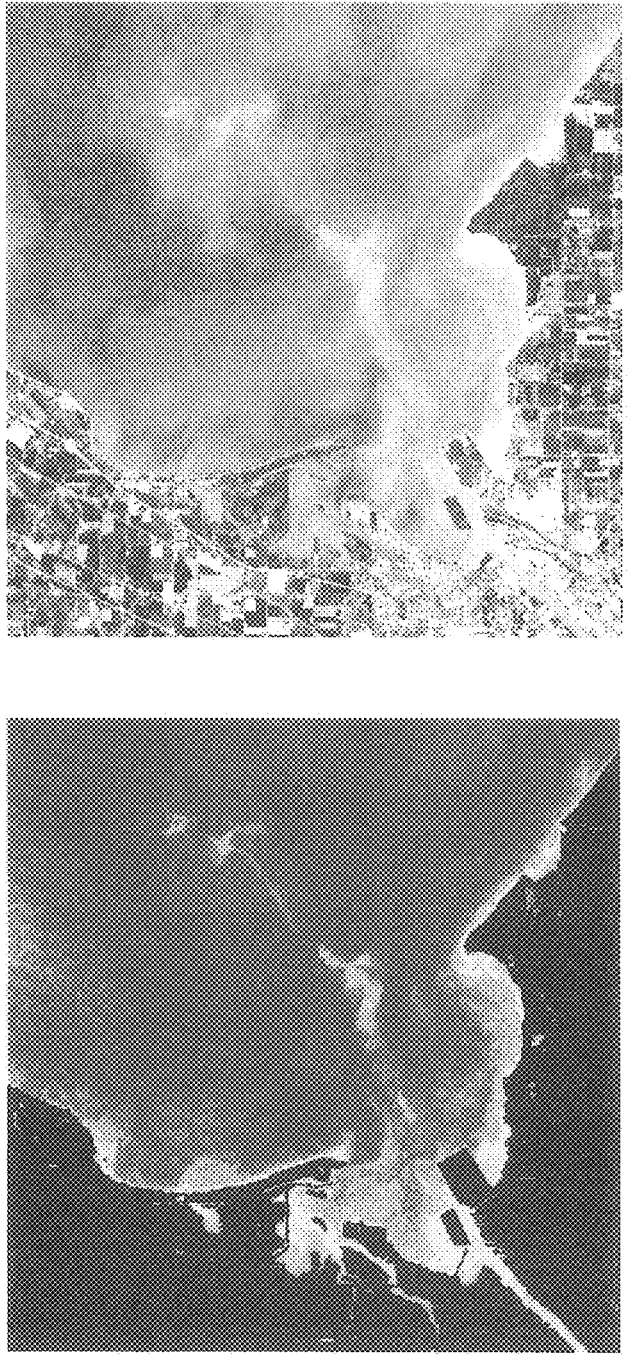
FIG. 2 is a photograph illustrating the LANDSAT 7 TM natural color (right) and total coliform (left) images (redder being greater) of SW Lake Erie (form LANDSAT TM data) in accordance with one embodiment of the present invention.

FIG. 2 is a photograph illustrating the LANDSAT 7 TM natural color (right) and total coliform (left) images (redder being greater) of SW Lake Erie (from LANDSAT TM data) in accordance with one embodiment of the present invention.

Figure 3:
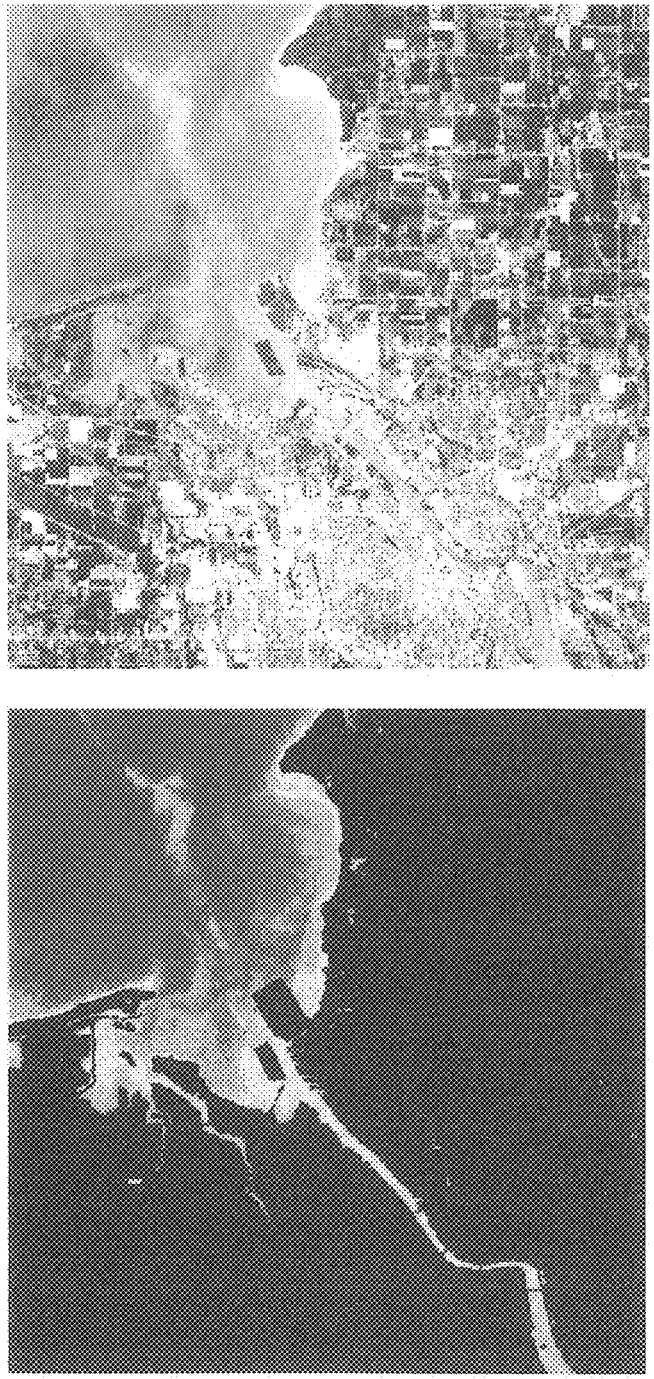
FIG. 3 is a photograph illustrating coliform mapping (red means more) from LANDSAT TM: Subarea 2, Maumee Bay (Toledo and Maumee, Ohio) in accordance with one embodiment of the present invention.
Figure 4:
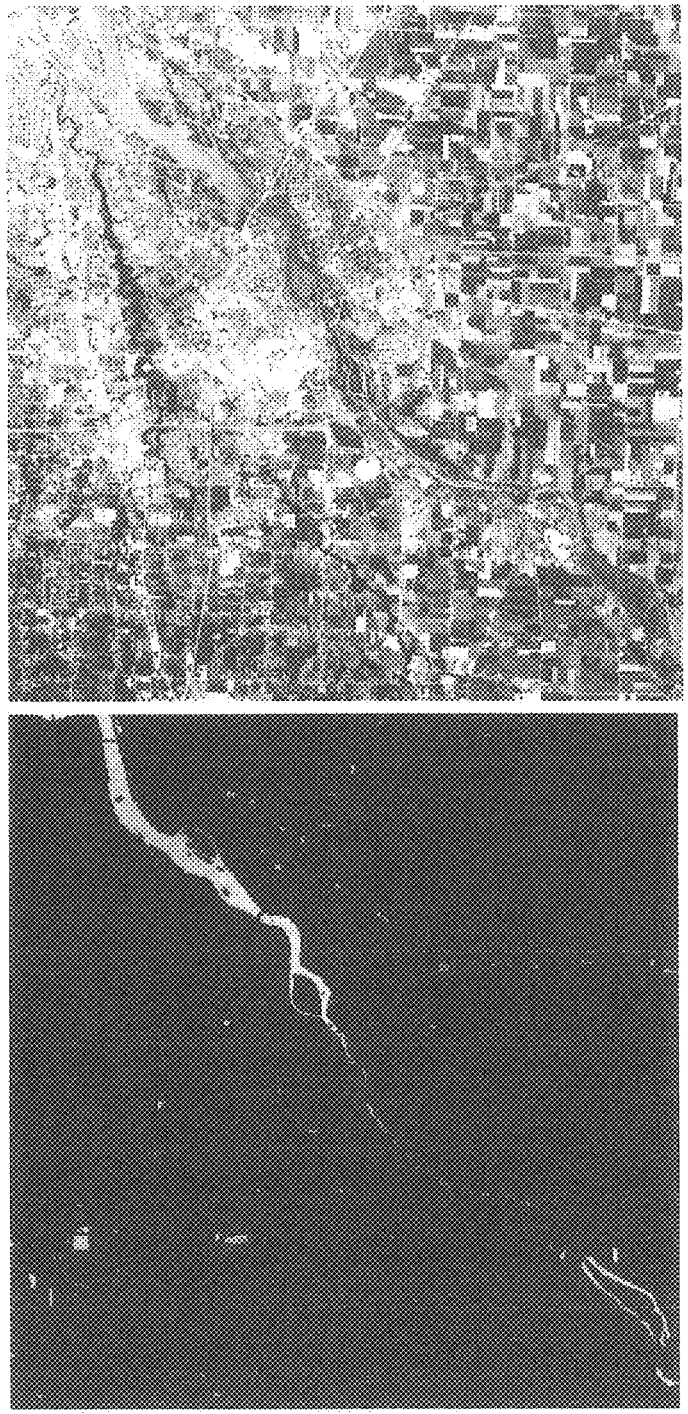
FIG. 4 is a photograph illustrating Coliform mapping (red means more) from LANDSAT TM: Subarea 3, Upper Maumee (Waterville, Ohio) in accordance with one embodiment of the present invention.
Figure 5:
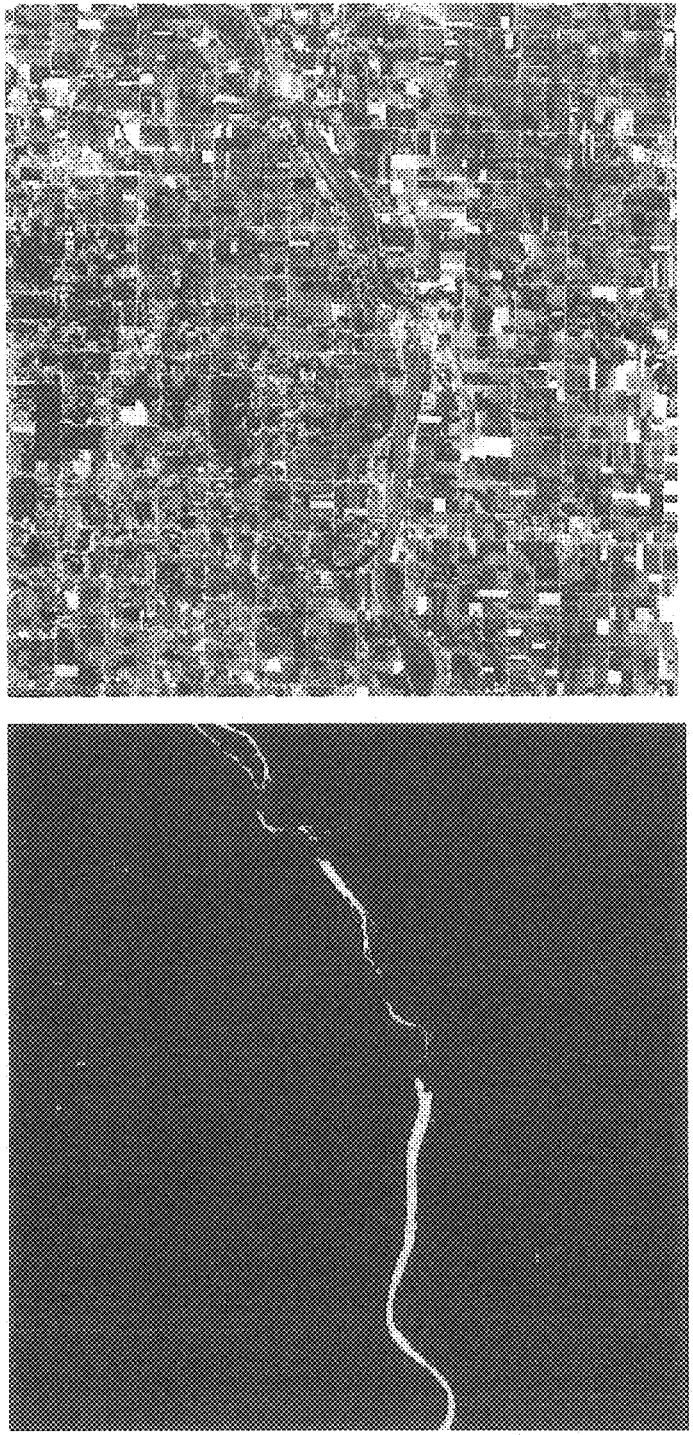
FIG. 5 is a photograph illustrating coliform mapping (red means more) from LANDSAT TM: Subarea 4, Low. Mid. Maumee (Grand Rapids, Ohio) in accordance with one embodiment of the present invention.
Figure 6:
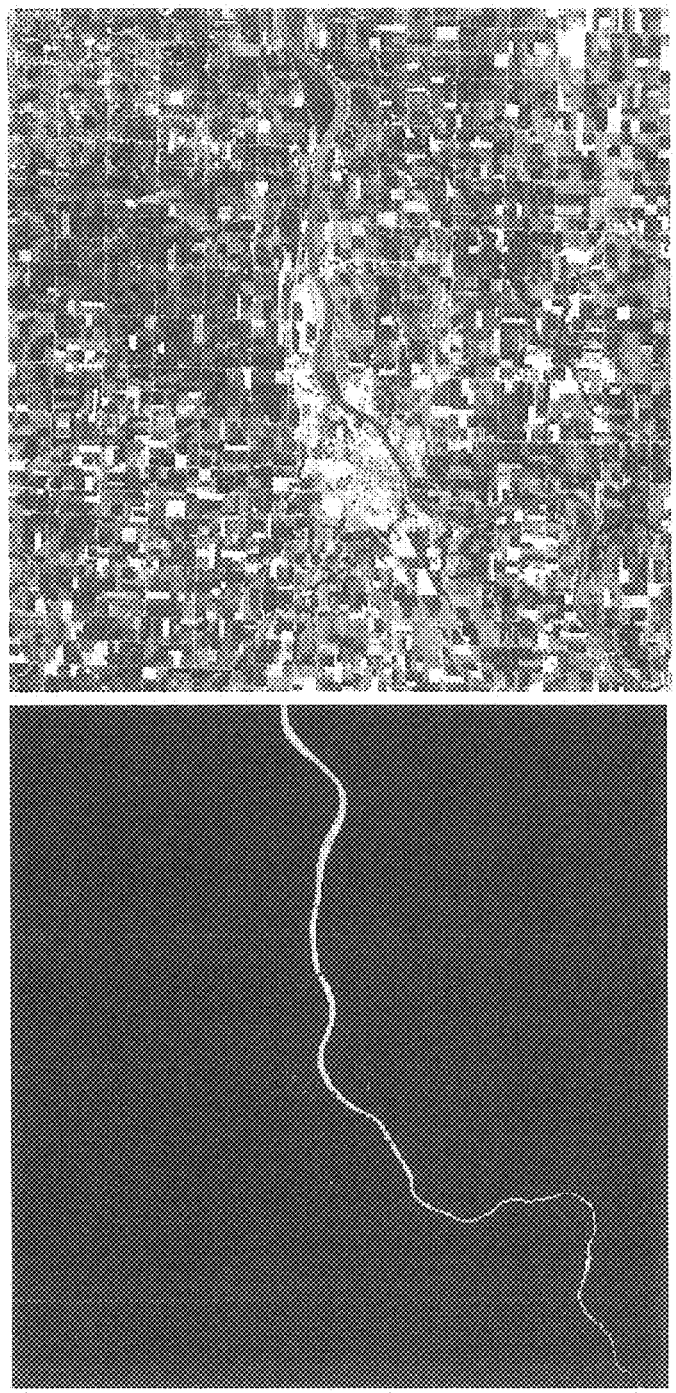
FIG. 6 is a photograph illustrating coliform mapping (red means more) from LANDSAT TM: Subarea 5, Up. Mid. Maumee (Napoleon, Ohio) in accordance with one embodiment of the present invention.
Figure 7:
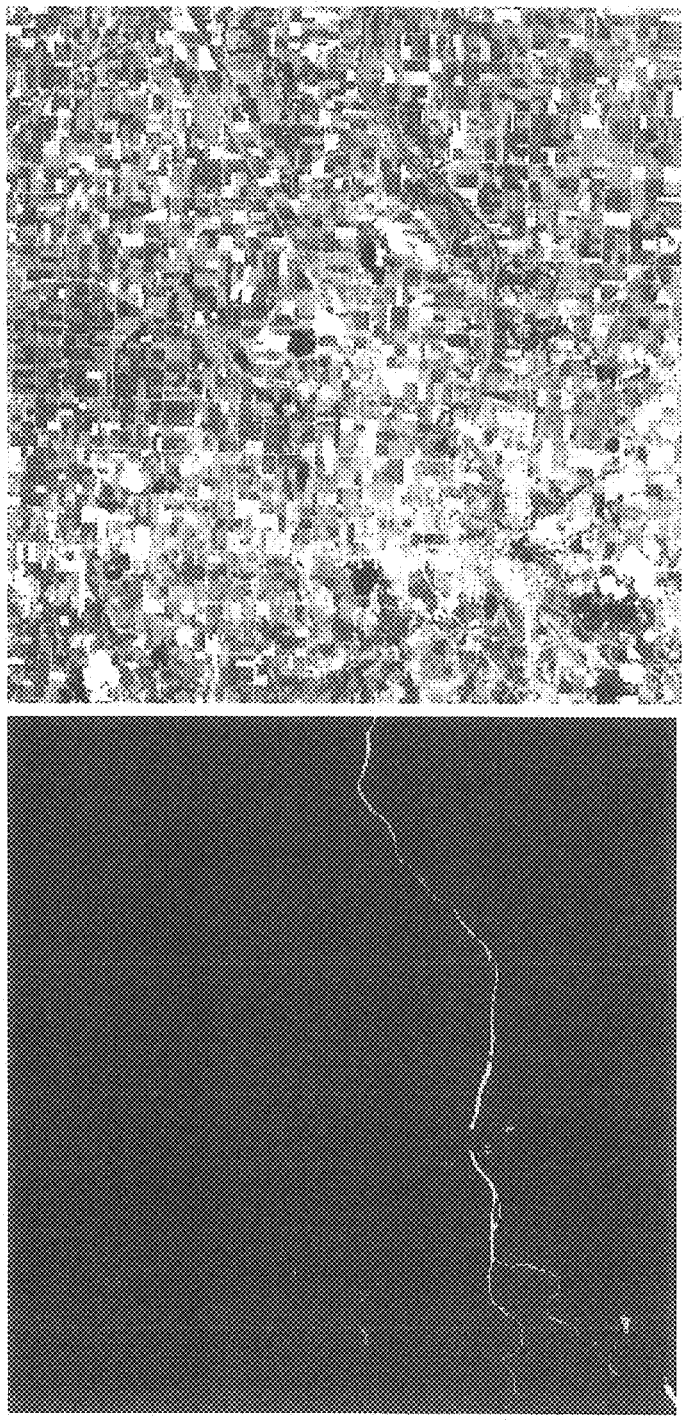
FIG. 7 is a photograph illustrating coliform mapping (red means more) from LANDSAT TM: Subarea 6, Lower Maumee (Defiance, Ohio) in accordance with one embodiment of the present invention.
Figure 8:
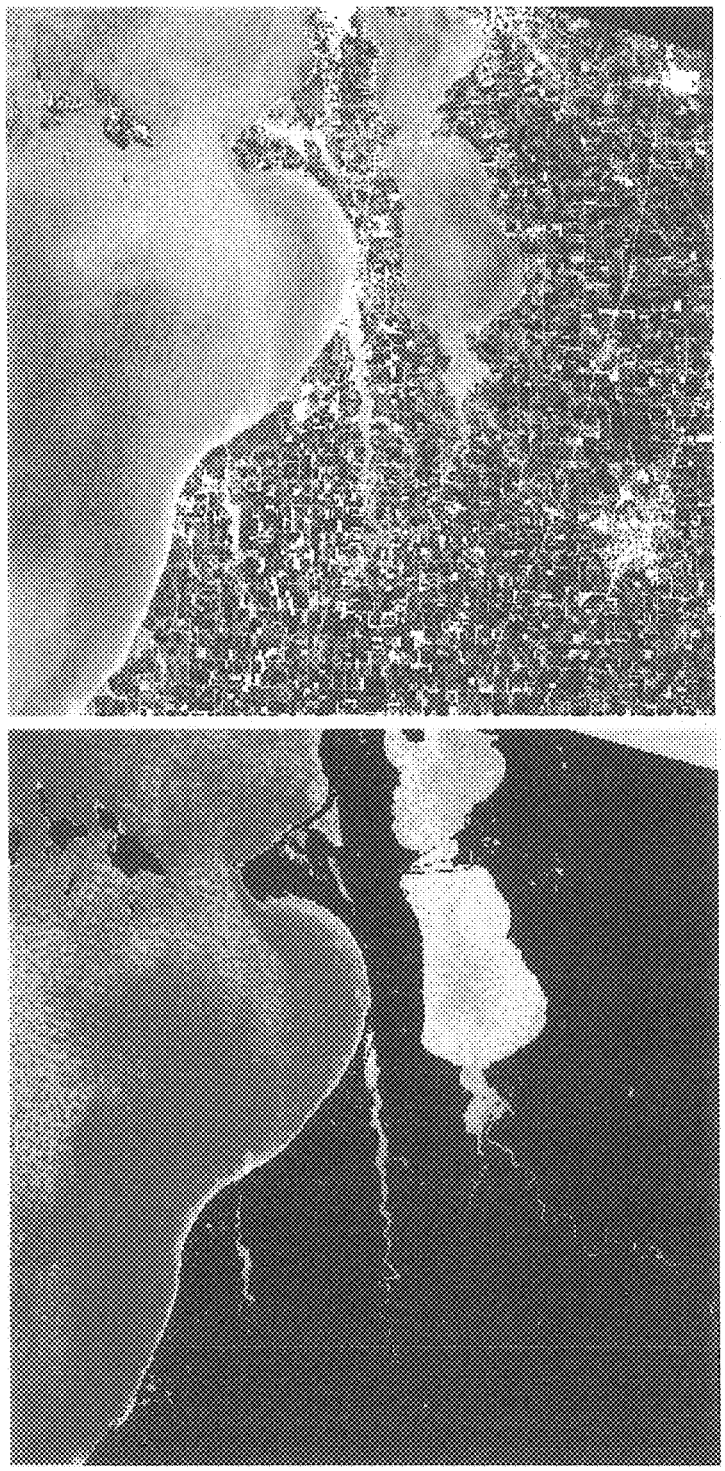
FIG. 8 is a photograph illustrating coliform mapping (red means more) from LANDSAT TM: Sandusky Bay, with Portage River in Image Center, in accordance with one embodiment of the present invention.
Figure 9:
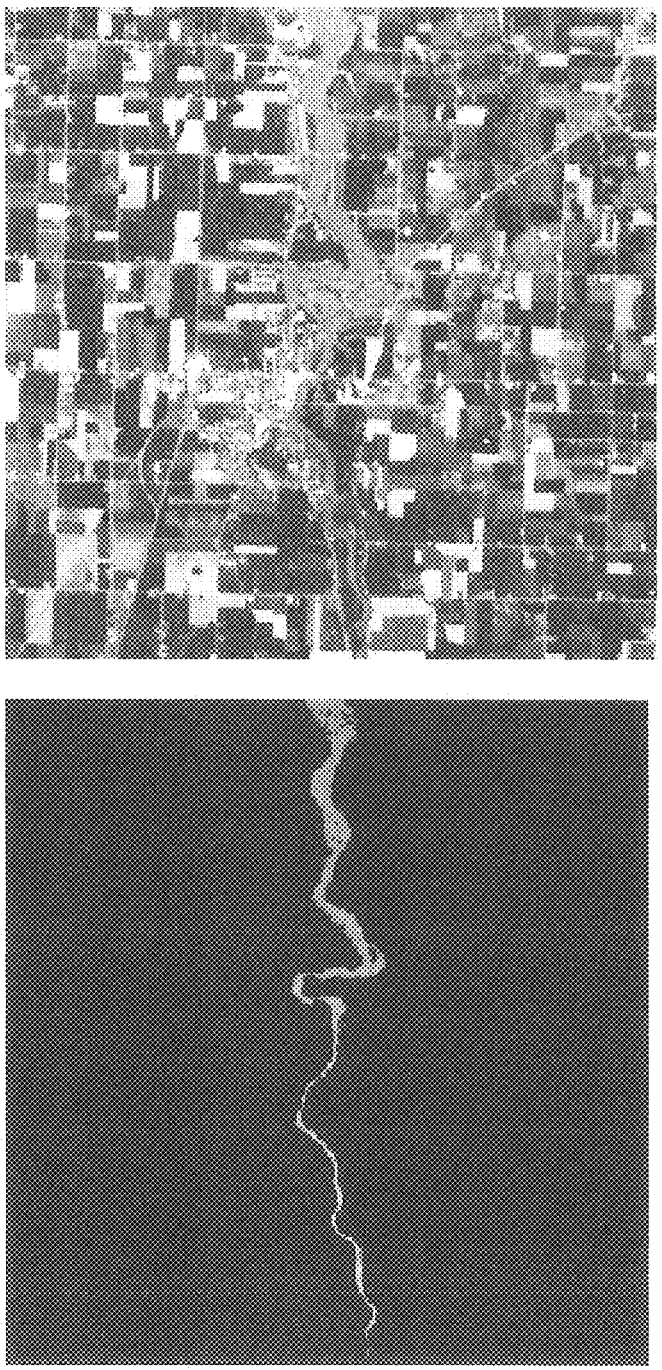
FIG. 9 is a photograph illustrating coliform mapping (red means more) from LANDSAT TM: Subarea 7, Oak Harbor, Ohio on the Portage River in accordance with one embodiment of the present invention.
Figure 10:
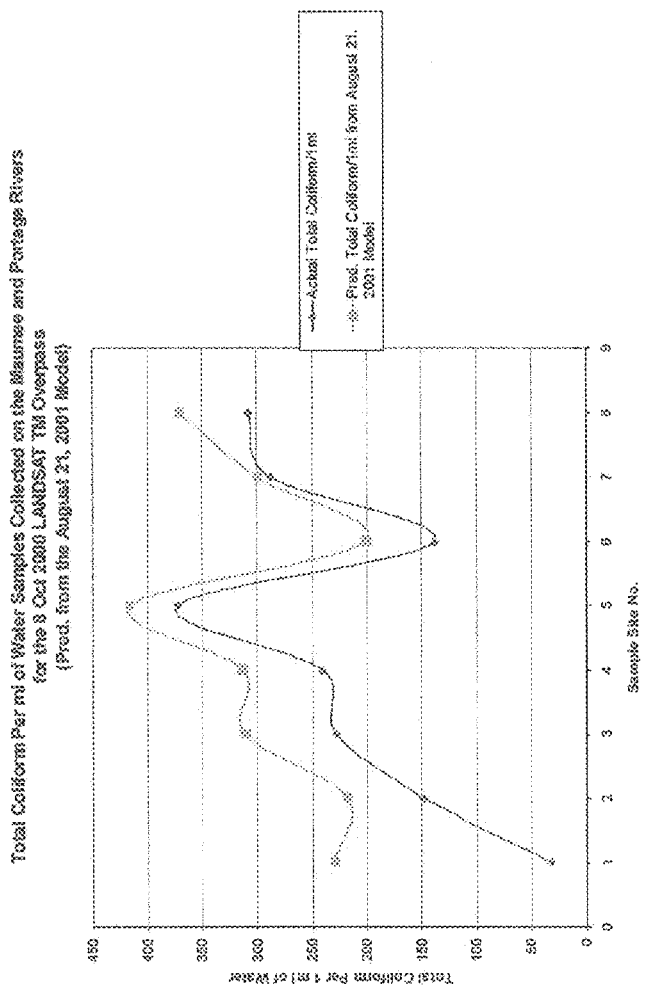
FIG. 10 is a graph of the total coliform model of Aug. 21, 2001 applied to water samples collected from Maumee and Portage Rivers on Oct. 8, 2000.
Figure 11:
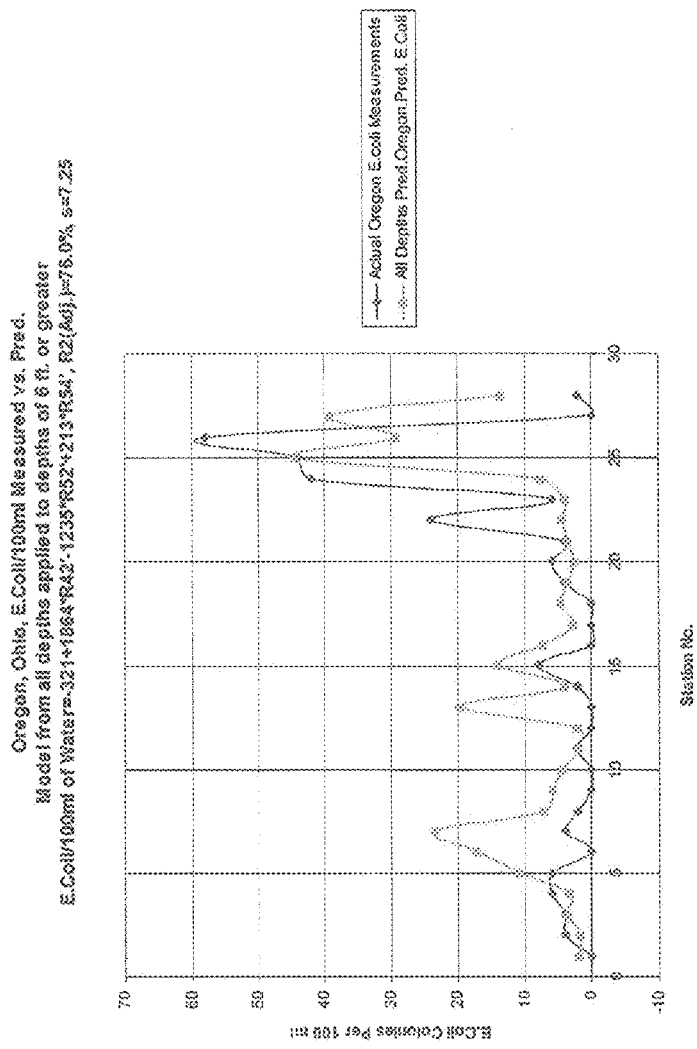
FIG. 11 is a graph of E. Coli model from the city of Oregon Data and LANDSAT TM data collected on Aug. 21, 2001 (samples from all water depths)
Figure 12:
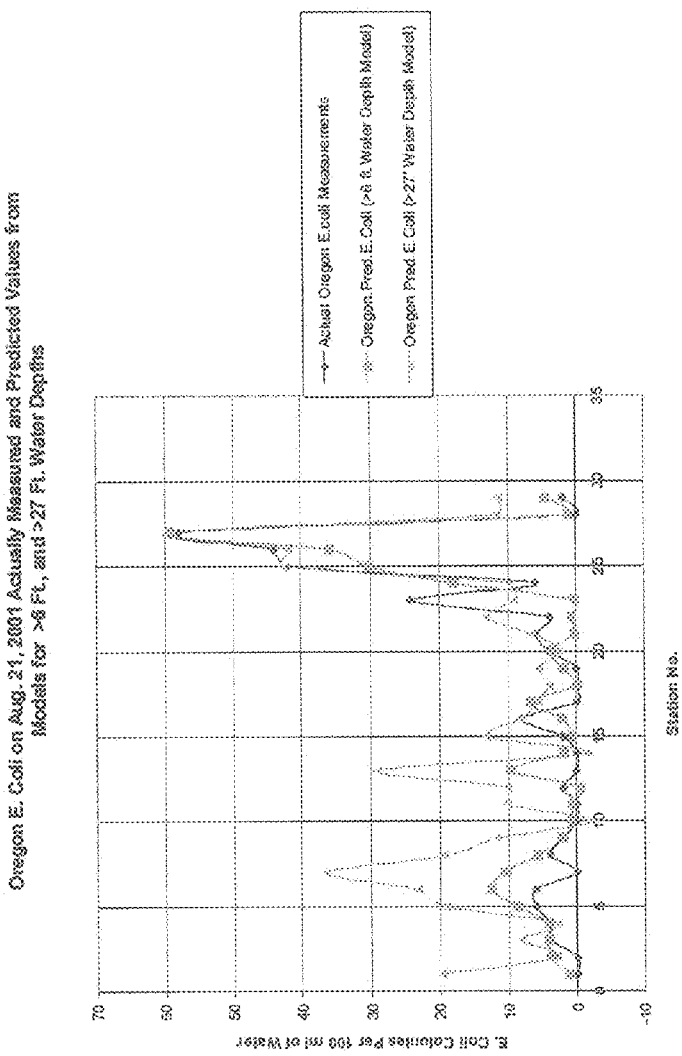
FIG. 12 is a graph of E. Coli model from the city of Oregon, Ohio with data in Maumee Bay for Aug. 21, 2001, for samples from >6 ft. and >27 ft. water depths.
Figure 13:
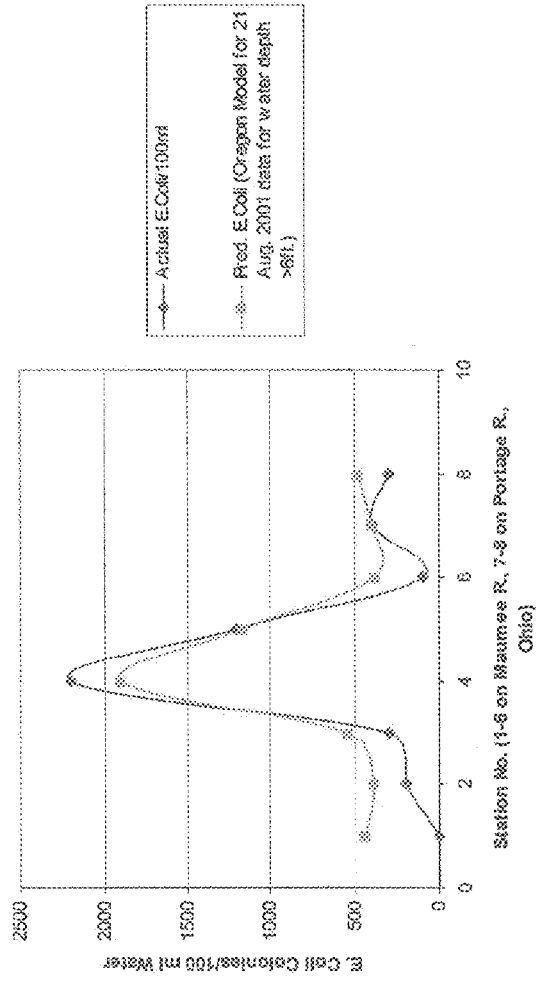
FIG. 13 is a graph of E. Coli model (>6 ft. water depth) of Oregon water samples collected on Aug. 21, 2001 applied to water samples collected from Maumee and Portage Rivers on Oct. 8, 2000.
Figure 14:
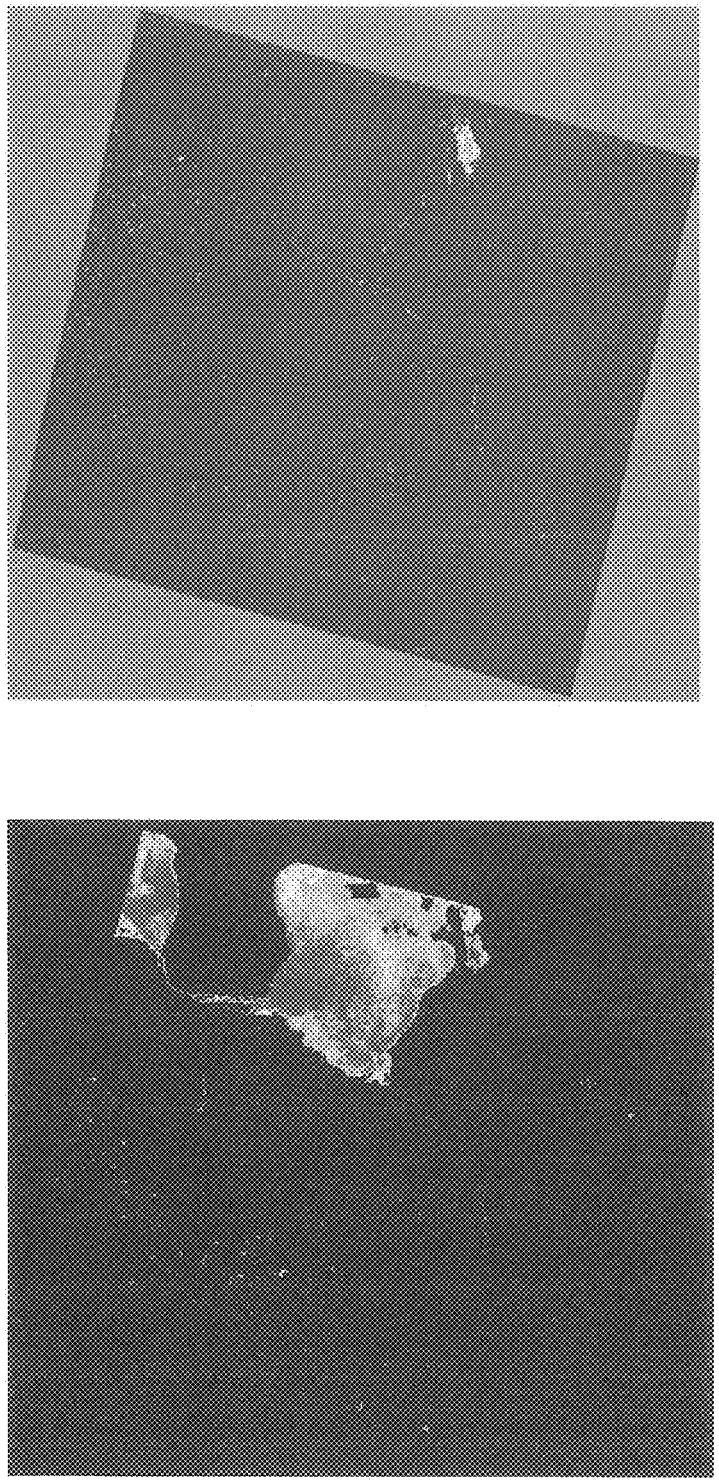
FIG. 14 includes photographs illustrating total coliform (left) and E. Coli (right) models of Aug. 21, 2001 from Lake Erie and Oregon, Ohio; data Applied to LANDSAT TM data of the same date, in accordance with one embodiment of the present invention.
Figure 15:
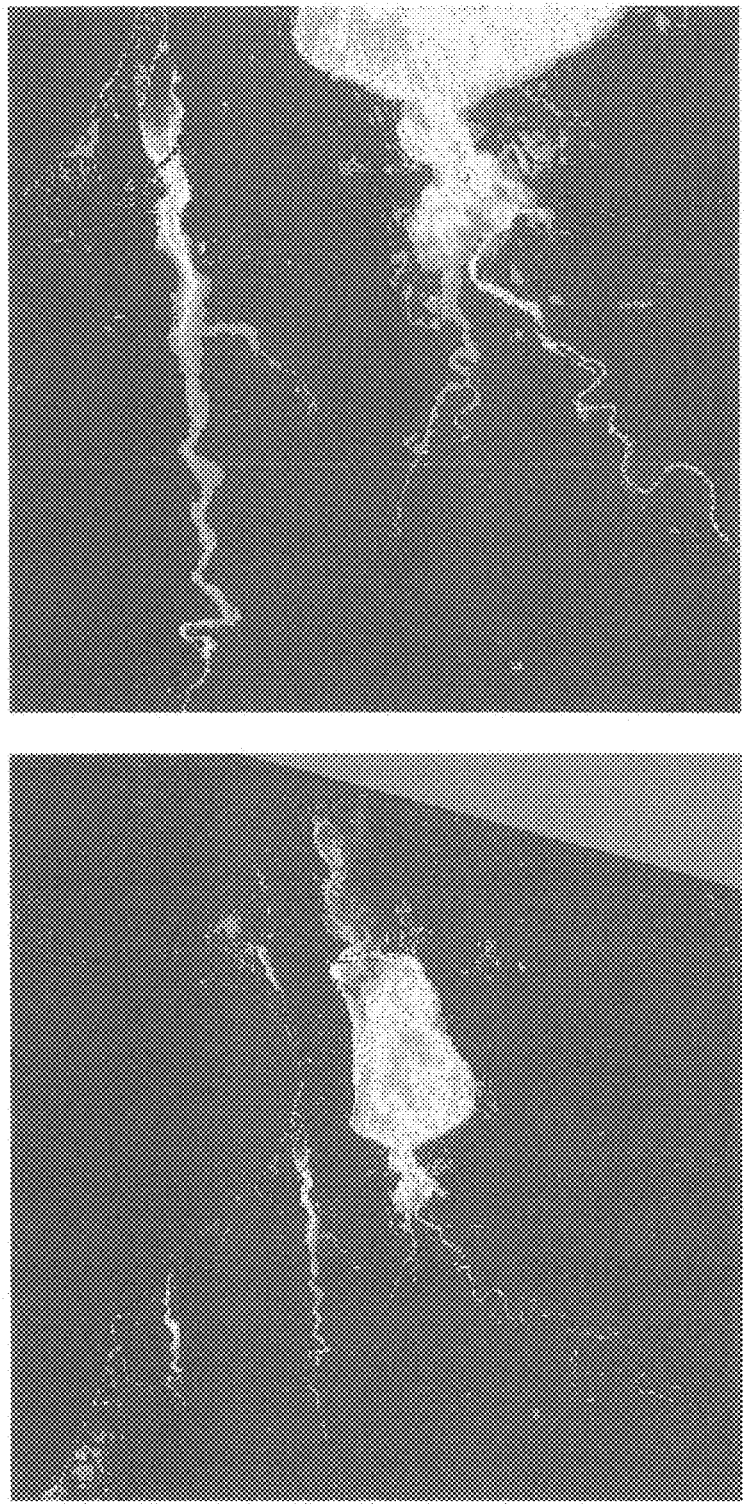
FIG. 15 includes photographs illustrating zoomed E. Coli images of Portage and Sandusky Rivers of Aug. 21, 2001 from LANDSAT TM data, in accordance with one embodiment of the present invention.
Figure 16:
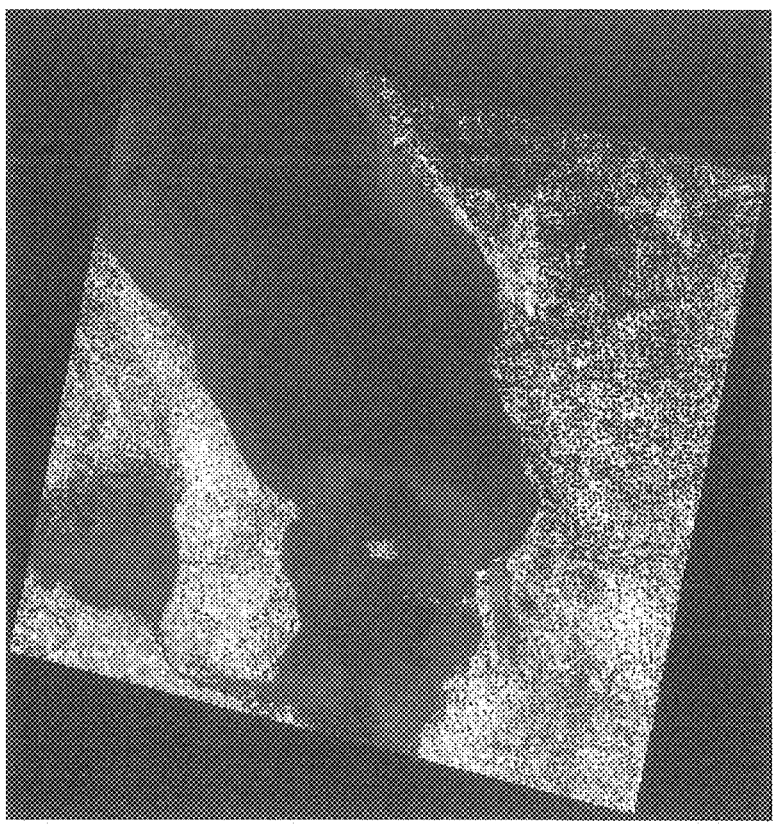
FIG. 16 is a photograph illustrating a natural color image of Lake Erie on 16 Jul. 2002 (Including Cleveland, Ohio)
Figure 17:
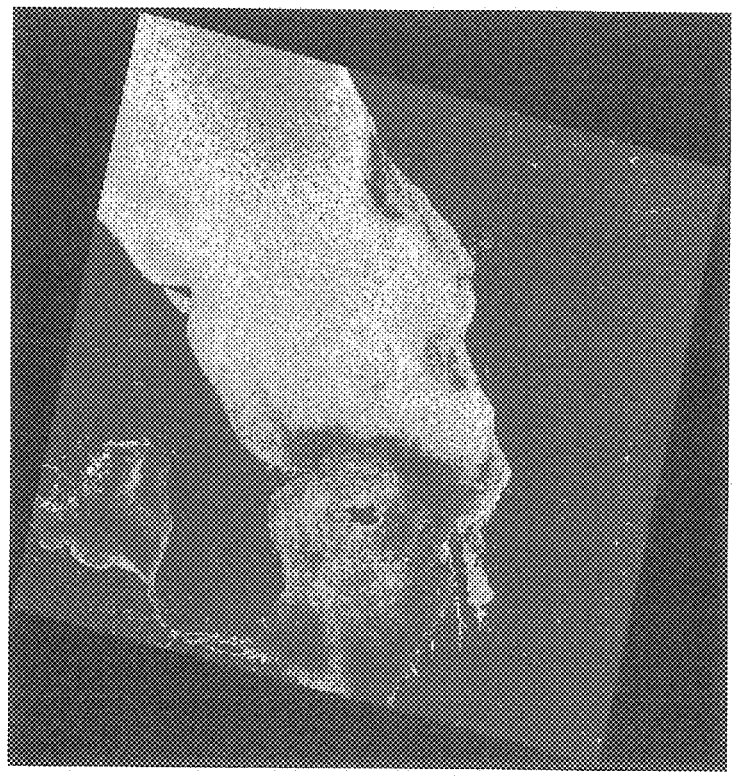
FIG. 17 is an overpass photograph illustrating Coliform Bacteria of Jul. 16, 2002 using an Aug. 21, 2001 model in accordance with one embodiment of the present invention.
Figure 18:
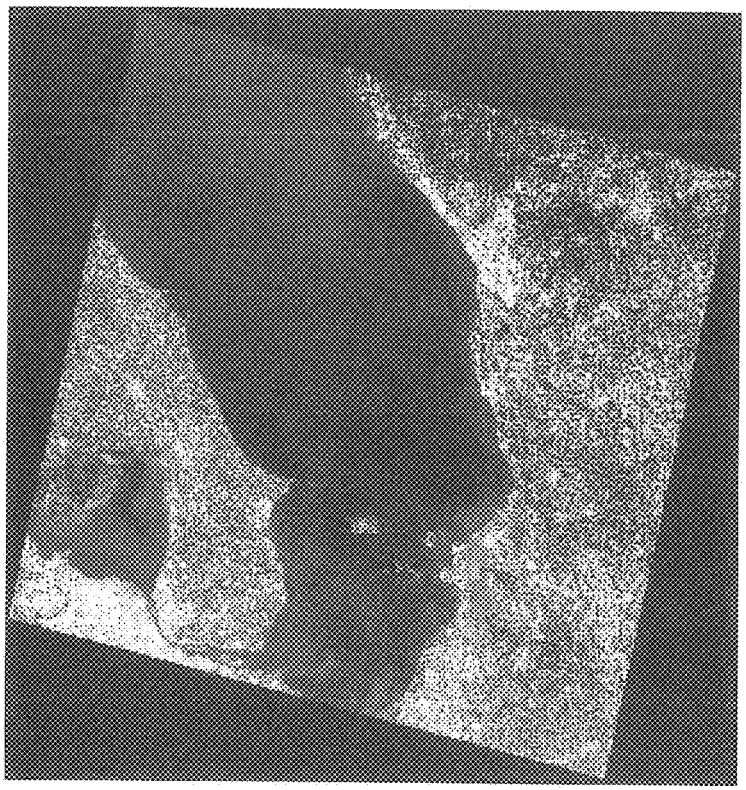
FIG. 18 is a photograph illustrating a natural color image of P. 19, R. 31 for 2 Aug. 2002 L7 Overpass.
Figure 19:
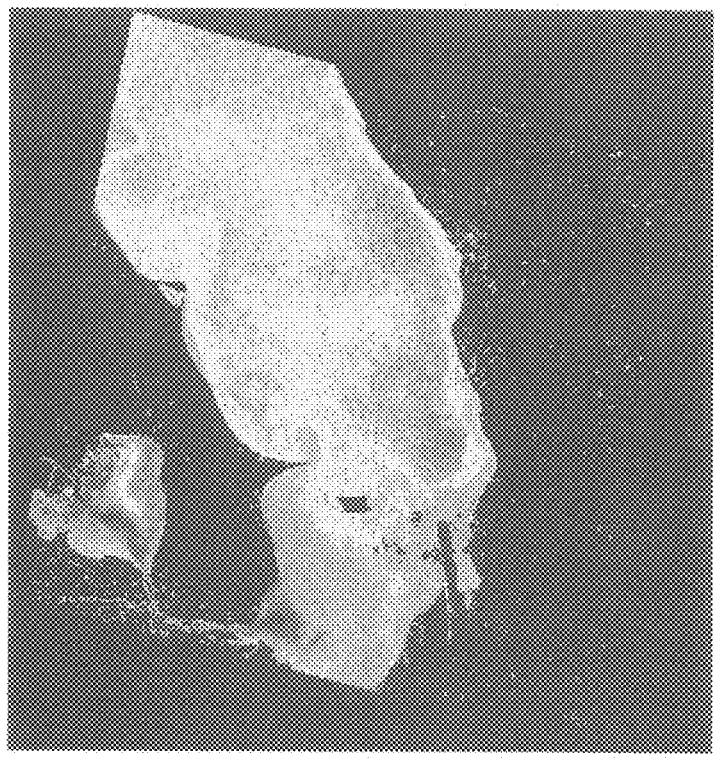
FIG. 19 is an overpass photograph illustrating Coliform Bacteria of Aug. 2, 2002 using an Aug. 21, 2001 model in accordance with one embodiment of the present invention.
Figure 20:
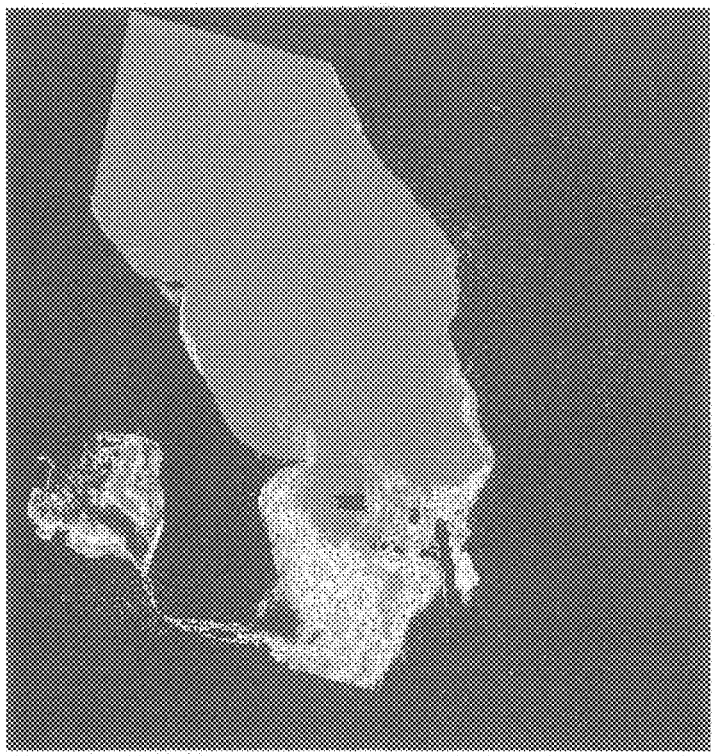
FIG. 20 is an overpass photograph illustrating Coliform Bacteria of Aug. 2, 2002 using a Jul. 16, 2001 stretch in accordance with one embodiment of the present invention.
Figure 21:
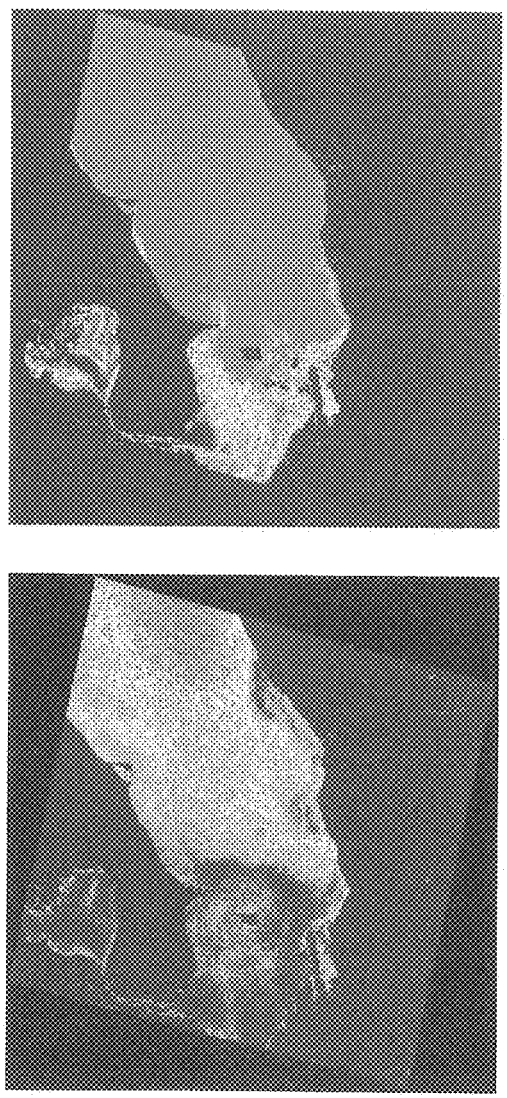
FIG. 21 includes photographs illustrating Coliform Bacteria for Jul. 16, 2002 (Left) and Aug. 2, 2002 (Right) Overpasses, Path 20-Row 31 (21 Aug. 2001 Model; with red representing 210-1710 colonies/ml in both images), in accordance with one embodiment of the present invention.

FIG. 3 is a photograph illustrating coliform mapping (red means more) from LANDSAT TM: Subarea 2, Maumee Bay (Toledo and Maumee, Ohio) in accordance with one embodiment of the present invention;

FIG. 4 is a photograph illustrating Coliform mapping (red means more) from LANDSAT TM: Subarea 3, Upper Maumee (Waterville, Ohio) in accordance with one embodiment of the present invention;

FIG. 5 is a photograph illustrating coliform mapping (red means more) from LANDSAT TM: Subarea 4, Low. Mid. Maumee (Grand Rapids, Ohio) in accordance with one embodiment of the present invention;

FIG. 6 is a photograph illustrating coliform mapping (red means more) from LANDSAT TM: Subarea 5, Up. Mid. Maumee (Napoleon, Ohio) in accordance with one embodiment of the present invention;

FIG. 7 is a photograph illustrating coliform mapping (red means more) from LANDSAT TM: Subarea 6, Lower Maumee (Defiance, Ohio) in accordance with one embodiment of the present invention;

FIG. 8 is a photograph illustrating coliform mapping (red means more) from LANDSAT TM: Sandusky Bay, with Portage River in Image Center, in accordance with one embodiment of the present invention;

FIG. 9 is a photograph illustrating coliform mapping (red means more) from LANDSAT TM: Subarea 7, Oak Harbor, Ohio on the Portage River in accordance with one embodiment of the present invention;

FIG. 10 is a graph of the total coliform model of Aug. 21, 2001 applied to water samples collected from Maumee and Portage Rivers on Oct. 8, 2000;

FIG. 11 is a graph of *E. Coli* model from the city of Oregon Data and LANDSAT TM data collected on Aug. 21, 2001 (samples from all water depths);

FIG. 12 is a graph of *E. Coli* model from the city of Oregon, Ohio with data in Maumee Bay for Aug. 21, 2001, for samples from >6 ft. and >27 ft. water depths;

FIG. 13 is a graph of *E. Coli* model (>6 ft. water depth) of Oregon water samples collected on Aug. 21, 2001 applied to water samples collected from Maumee and Portage Rivers on Oct. 8, 2000;

FIG. 14 includes photographs illustrating total coliform (left) and *E. Coli* (right) models of Aug. 21, 2001 from Lake Erie and Oregon, Ohio; data Applied to LANDSAT TM data of the same date, in accordance with one embodiment of the present invention;

FIG. 15 includes photographs illustrating zoomed *E. Coli* images of Portage and Sandusky Rivers of Aug. 21, 2001 from LANDSAT TM data, in accordance with one embodiment of the present invention;

FIG. 16 is a photograph illustrating a natural color image of Lake Erie on 16 Jul. 2002 (Including Cleveland, Ohio);

FIG. 17 is an overpass photograph illustrating Coliform Bacteria of Jul. 16, 2002 using an Aug. 21, 2001 model in accordance with one embodiment of the present invention;

FIG. 18 is a photograph illustrating a natural color image of P. 19, R. 31 for 2 Aug. 2002 L7 Overpass;

FIG. 19 is an overpass photograph illustrating Coliform Bacteria of Aug. 2, 2002 using an Aug. 21, 2001 model in accordance with one embodiment of the present invention;

FIG. 20 is an overpass photograph illustrating Coliform Bacteria of Aug. 2, 2002 using a Jul. 16, 2001 stretch in accordance with one embodiment of the present invention; and FIG. 21 includes photographs illustrating Coliform Bacteria for Jul. 16, 2002 (Left) and Aug. 2, 2002 (Right) Overpasses, Path 20-Row 31 (21 Aug. 2001 Model; with red representing 210-1710 colonies/ml in both images), in accordance with one embodiment of the present invention.

The color key for the total coliform assay data shown in FIGS. 2-9, 14:

| Color | Colonies (Coliform) per 100 Ml of Water |
|---|---|
| Red | 14000-18300 |
| Orange | 10800-13900 |
| Yellow | 10200-10700 |
| Yellow-Green | 9600-10100 |
| Green | 7000-9000 |
| All Blues | 0-6900 |

The color key for the *E. Coli* assay data shown in FIGS. 14 and 15:

| Color | Colonies (Coliform) per 100 Ml of Water |
|---|---|
| Red | 224-380 |
| Orange | 171-223 |
| Yellow | 160-170 |
| Yellow-Green | 141-159 |
| Green | 111-140 |
| All Blues | 0-110 |

Visual inspection of the water samples, particularly one collected during a microcystis bloom on Aug. 19, 2003, and with the aid of a microscope revealed bacteria range from 0.5-1.0 micrometers in size, and I don't know if we are observing them directly or whether we are seeing what they feed on (such as fecal matter) in the water.

The wavelengths of light in bands 2, 3, and 4 are about the size of bacteria, so it is at least possible that it is the bacteria themselves that are being detected by the coliform and *E. coli* algorithms, but it will take some lab experimentation to prove what is being mapped by the algorithms. However, the models clearly show that the predicted and actual values of coliform content in one case and *E. coli* content in the other case are pretty well correlated.

Unlike the preferred phycocyanin and *E. coli* algorithms, the preferred coliform algorithm only uses spectral ratios of TM bands 2, 3, and 4, which are in the wavelength range of silicon detectors. Therefore, very inexpensive sensors are available, such as the ones used for video cameras. The algorithms for *E. coli* and phycocyanin, however, require use of TM bands 5 and/or 7, and they can be done with more expensive sensors on or near the Earth's surface.

Having shown and described a preferred embodiment of the invention, those skilled in the art will realize that many variations and modifications may be made to affect the described invention and still be within the scope of the claimed invention. Thus, many of the elements indicated above may be altered or replaced by different elements which will provide the same result and fall within the spirit of the claimed invention. It is the intention, therefore, to limit the invention only as indicated by the scope of the claims.

What is claimed is:

1. A method of determining the presence of *E. coli* in water from light reflected therefrom, said method comprising the steps of:
    (a) obtaining a measurement of reflected light from said water, said measurement comprising a measurement of the respective amount of light in at least three frequency ranges: (i) from about 0.52 μm to about 0.60 μm; (ii) from about 0.76 μm to about 0.90 m; and (iii) from about 1.55 μm to about 1.75 μm; and
    (b) relating the approximate amount of said *E. coli* in said water to said respective amounts of light by applying an algorithm relating said respective amounts of light in said at least three frequency ranges to the amount of *E. coli* colonies in said water by using at least one ratio between two of said at least three frequency ranges.

2. A method according to claim 1 wherein said measurement of the amount of light in said at least three frequency ranges comprises the measurement, respectively, of: (i) LANDSAT TM band 2, (ii) LANDSAT TM band 4, and (iii) LANDSAT TM band 5.

3. A method according to claim 1 wherein said algorithm is any algorithm selected from the group consisting of $X \approx K_1 + K_2 \times (R42) - K_3 \times (R52) + K_4 \times (R54)$ and equivalents wherein:
    X is the approximate amount of *E. Coli* expressed in colonies per 100 ml;
    $K_1$ is a value in the range of from about −220 to about −420;
    $K_2$ is a value in the range of from about 1750 to about 1950;
    $K_3$ is a value in the range of from about 1130 to about 1330;
    $K_4$ is a value in the range of from about 100 to about 300;
    R42 is the value of LANDSAT TM band 4 divided by LANDSAT TM band 2, after subtraction for atmospheric haze separately in each band;
    R52 is the value of LANDSAT TM band 5 divided by LANDSAT TM band 2, after subtraction for atmospheric haze separately in each band; and
    R54 is the value of LANDSAT TM band 5 divided by LANDSAT TM band 4, after subtraction for atmospheric haze separately in each band.

4. A method according to claim 3 wherein:
    $K_1$ is a value in the range of from about −300 to about −400;
    $K_2$ is a value in the range of from about 1825 to about 1875;
    $K_3$ is a value in the range of from about 1170 to about 1290;
    $K_4$ is a value in the range of from about 175 to about 250.

5. A method according to claim 3 wherein:
    $K_1$ is a value in the range of from about −310 to about −330;
    $K_2$ is a value in the range of from about 1860 to about 1870;
    $K_3$ is a value in the range of from about 1220 to about 1250; and
    $K_4$ is a value in the range of from about 200 to about 220.

6. A method according to claim 1 wherein the calculated value of *E. coli* correlates to the actual measured amount of said *E. coli* in said water by a correlation value in excess of 60%.

7. A method according to claim 1 wherein the calculated value of *E. coli* correlates to the actual measured amount of said *E. coli* in said water by a correlation value in excess of 70%.

8. A method according to claim 5 wherein the calculated value of X correlates to the actual measured amount of said *E. coli* in said water by a correlation value in excess of 60%.

9. A method according to claim 5 wherein the calculated value of X correlates to the actual measured amount of said *E. coli* in said water by a correlation value in excess of 70%.

10. A method according to claim 1 additionally comprising the step of transmitting data relating to the approximate amount of said *E. coli* in said water to a site remote from the site where said measurement takes place.

11. A method according to claim 5 additionally comprising the step of transmitting data relating to the approximate amount of said *E. coli* in said water to a site remote from the site where said measurement takes place.

12. A method according to claim 1 additionally comprising the step of generating a report of said approximate amount of said *E. coli*.

13. A method according to claim 1 additionally comprising the step of transmitting data relating to the approximate amount of said *E. coli* expressed in micrograms per liter in said water to a site remote from the site where said measurement takes place.

14. A method of determining the presence of *E. coli* in water from light reflected therefrom, said method comprising the steps of:
    (a) obtaining a measurement of reflected light from said water, said measurement comprising a measurement of the respective amount of light in at least three frequencies comprising, respectively: (i) LANDSAT TM band 2, (ii) LANDSAT TM band 3, and (iii) LANDSAT TM band 5; and (b) relating the approximate amount of said *E. Coli* in said water to said respective amounts of light by applying an algorithm relating said respective amounts of light in said at least three frequency ranges to the amount of *E. coli* in said water, wherein said algorithm is any algorithm selected from the group consisting of $X \approx K_1 + K_2 \times (R42) - K_3 \times (R52) + K_4 \times (R54)$ and equivalents wherein:
    X is the approximate amount of *E. coli* expressed in colonies per 100 ml;
    $K_1$ is a value of about −321;
    $K_2$ is a value of about 1864;
    $K_3$ is a value of about 1235;
    $K_4$ is a value of about 213;
    R42 is the value of LANDSAT TM band 4 divided by LANDSAT TM band 2, after subtraction for atmospheric haze separately in each band;
    R52 is the value of LANDSAT TM band 5 divided by LANDSAT TM band 2, after subtraction for atmospheric haze separately in each band; and
    R54 is the value of LANDSAT TM band 5 divided by LANDSAT TM band 4, after subtraction for atmospheric haze separately in each band.

15. A system for determining the presence of *E. coli* in water from light reflected therefrom, said device comprising:
    (a) a measurement device adapted to measure reflected light from said water, said measurement comprising a measurement of the respective amount of light in at least three frequency ranges: (i) from about 0.52 μm to about 0.60 μm; (ii) from about 0.76 μm to about 0.90 m; and (iii) from about 1.55 μm to about 1.75 μm; and
    (b) a processor at said remote site and capable of relating the approximate amount of said *E. coli* in said water to said respective amounts of light by applying an algorithm relating said respective amounts of light in said at least three frequency ranges to the amount of *E. Coli* in said water by using at least one ratio between two of said at least three frequency ranges.

* * * * *